United States Patent
Allan et al.

(10) Patent No.: US 9,416,182 B2
(45) Date of Patent: Aug. 16, 2016

(54) ANTI-TNF-ANTI-IL-17 BISPECIFIC ANTIBODIES

(71) Applicant: Eli Lilly and Company, Indianapolis, IN (US)

(72) Inventors: Barrett Allan, Encinitas, CA (US); Andrew Lawrence Glasebrook, San Diego, CA (US); Jirong Lu, Carmel, IN (US); Ying Tang, San Diego, CA (US); Derrick Ryan Witcher, Fishers, IN (US); Donmienne Doen Mun Leung, San Diego, CA (US); Pia Pauliina Yachi, San Diego, CA (US); Andrew Charles Vendel, Cardiff-by-the-Sea, CA (US)

(73) Assignee: Eli Lilly and Company, Indianapolis, IN (US)

( * ) Notice: Subject to any disclaimer, the term of this patent is extended or adjusted under 35 U.S.C. 154(b) by 123 days.

(21) Appl. No.: 14/195,885

(22) Filed: Mar. 4, 2014

(65) Prior Publication Data

US 2014/0255406 A1    Sep. 11, 2014

Related U.S. Application Data

(60) Provisional application No. 61/774,909, filed on Mar. 8, 2013.

(51) Int. Cl.
| | |
|---|---|
| *C07K 16/00* | (2006.01) |
| *A61K 39/395* | (2006.01) |
| *A61K 39/40* | (2006.01) |
| *C07K 16/24* | (2006.01) |
| *C07K 1/00* | (2006.01) |
| *A61K 39/00* | (2006.01) |

(52) U.S. Cl.
CPC ............. *C07K 16/244* (2013.01); *C07K 16/241* (2013.01); *A61K 2039/505* (2013.01); *C07K 2317/31* (2013.01); *C07K 2317/622* (2013.01); *C07K 2317/76* (2013.01)

(58) Field of Classification Search
None
See application file for complete search history.

(56) References Cited

U.S. PATENT DOCUMENTS

| 6,090,382 A | 7/2000 | Salfeld et al. |
| 2009/0163699 A1 | 6/2009 | Chamberlain |

FOREIGN PATENT DOCUMENTS

| WO | 95/09917 | 4/1995 |
| WO | 2007/070750 | 6/2007 |
| WO | 2010/102251 | 9/2010 |
| WO | 2013158577 | 10/2013 |

OTHER PUBLICATIONS

Colman et al. Research in Immunology, 1994; 145(1): 33-36.*
Fisher et al. Arthritis & Rheumatology 2015, 67;1:51-62.*
Patent Cooperation Treaty International Search Report and Written Opinion for International Application No. PCT/US2014/020062; date of mailing Jun. 30, 2014.
Koenders, Marije I., et al., "Tumor Necrosis Factor-Interleukin-17 Interplay Induces S100A8, Interleukin-1 beta, and Matrix Metalloproteinases, and Drives Irreversible Cartilage Destruction in Murine Arthritis," Arthritis & Rheumatism, vol. 63, No. 8, Aug. 1, 2011, pp. 2329-2339.
Zhu, Shu, et al., "IL-17/IL-17 Receptor System in Autoimmune Disease: Mechanisms and Therapeutic Potential," Clinical Science, vol. 180, No. 11, Feb. 10, 2012, pp. 487-511.

* cited by examiner

*Primary Examiner* — Chun Dahle
(74) *Attorney, Agent, or Firm* — Gregory A. Cox

(57) ABSTRACT

Bispecific antibodies are provided that specifically bind both Tumor Necrosis Factor alpha (TNFα) and Interleukin-17 (IL-17). The bispecific antibodies of the invention are useful for treating various autoimmune diseases, including Rheumatoid Arthritis (RA), Psoriatic Arthritis (PsA), and Ankylosing Spondylitis (AS).

6 Claims, No Drawings

SEQUENCE LISTING

<160> NUMBER OF SEQ ID NOS: 4

<210> SEQ ID NO 1
<211> LENGTH: 712
<212> TYPE: PRT
<213> ORGANISM: Artificial Sequence
<220> FEATURE:
<223> OTHER INFORMATION: synthetic construct

<400> SEQUENCE: 1

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

```
Ala Met His Trp Val Arg Gln Ala Pro Gly Lys Gly Leu Glu Trp Val
         35                  40                  45

Ser Ala Ile Thr Trp Asn Ser Gly His Ile Asp Tyr Ala Asp Ser Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Ser Tyr Leu Ser Thr Ala Ser Ser Leu Asp Tyr Trp Gly
                100                 105                 110

Gln Gly Thr Leu Val Thr Val Ser Ser Ala Ser Thr Lys Gly Pro Ser
                115                 120                 125

Val Phe Pro Leu Ala Pro Cys Ser Arg Ser Thr Ser Glu Ser Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                    165                 170                 175

Val Leu Gln Ser Ser Gly Leu Tyr Ser Leu Ser Ser Val Val Thr Val
                180                 185                 190

Pro Ser Ser Ser Leu Gly Thr Lys Thr Tyr Thr Cys Asn Val Asp His
                195                 200                 205

Lys Pro Ser Asn Thr Lys Val Asp Lys Arg Val Glu Ser Lys Tyr Gly
            210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                    245                 250                 255

Thr Pro Glu Val Thr Cys Val Val Val Asp Val Ser Gln Glu Asp Pro
                260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Gly
            435                 440                 445
```

```
Gly Gly Ser Gly Gly Gly Ser Gly Gly Gly Ser Gln Val Gln
    450             455             460

Leu Val Gln Ser Gly Ala Glu Val Lys Lys Pro Gly Ser Ser Val Lys
465                 470                 475                 480

Val Ser Cys Lys Ala Ser Gly Tyr Lys Phe Thr Asp Tyr His Ile His
                485                 490                 495

Trp Val Arg Gln Ala Pro Gly Gln Cys Leu Glu Trp Met Gly Val Ile
            500                 505                 510

Asn Pro Thr Tyr Gly Thr Thr Asp Tyr Asn Gln Arg Phe Lys Gly Arg
        515                 520                 525

Val Thr Ile Thr Ala Asp Glu Ser Thr Ser Thr Ala Tyr Met Glu Leu
530                 535                 540

Ser Ser Leu Arg Ser Glu Asp Thr Ala Val Tyr Tyr Cys Ala Arg Tyr
545                 550                 555                 560

Asp Tyr Phe Thr Gly Thr Gly Val Tyr Trp Gly Gln Gly Thr Leu Val
                565                 570                 575

Thr Val Ser Ser Gly Gly Gly Gly Ser Gly Gly Gly Gly Ser Gly Gly
            580                 585                 590

Gly Gly Ser Gly Gly Gly Gly Ser Asp Ile Val Met Thr Gln Thr Pro
        595                 600                 605

Leu Ser Leu Ser Val Thr Pro Gly Gln Pro Ala Ser Ile Ser Cys Arg
610                 615                 620

Ser Ser Arg Ser Leu Val His Ser Arg Gly Glu Thr Tyr Leu His Trp
625                 630                 635                 640

Tyr Leu Gln Lys Pro Gly Gln Ser Pro Gln Leu Leu Ile Tyr Lys Val
                645                 650                 655

Ser Asn Arg Phe Ile Gly Val Pro Asp Arg Phe Ser Gly Ser Gly Ser
            660                 665                 670

Gly Thr Asp Phe Thr Leu Lys Ile Ser Arg Val Glu Ala Glu Asp Val
        675                 680                 685

Gly Val Tyr Tyr Cys Ser Gln Ser Thr His Leu Pro Phe Thr Phe Gly
        690                 695                 700

Cys Gly Thr Lys Leu Glu Ile Lys
705                 710

<210> SEQ ID NO 2
<211> LENGTH: 214
<212> TYPE: PRT
<213> ORGANISM: Artificial Sequence
<220> FEATURE:
<223> OTHER INFORMATION: synthetic construct

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95
```

```
Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 2136
<212> TYPE: DNA
<213> ORGANISM: Artificial Sequence
<220> FEATURE:
<223> OTHER INFORMATION: synthetic construct

<400> SEQUENCE: 3
```

| | | | | | |
|---|---|---|---|---|---|
| gaggtgcagc | tggtggagtc | tgggggaggc | ttggtacagc | ctggaggtc | cctgagactc | 60 |
| tcctgtgcag | cctctggatt | cacctttgat | gactatgcca | tgcactgggt | ccgccaggct | 120 |
| ccagggaagg | gctggagtg | gtgtcagct | attacttgga | atagtggtca | catagactac | 180 |
| gcagactccg | tgagggccg | gttcaccatc | tccagagaca | atgccaagaa | ctccctgtat | 240 |
| ctgcaaatga | acagcctgag | agccgaggac | acggccgtat | attactgtgc | gaaagtgagc | 300 |
| tacctgagta | ctgcctccag | cctggactac | tggggccaag | gaaccctggt | caccgtctcc | 360 |
| tcagcctcca | ccaagggccc | atcggtcttc | ccgctagcgc | cctgctccag | gagcacctcc | 420 |
| gagagcacag | ccgccctggg | ctgcctggtc | aaggactact | tccccgaacc | ggtgacggtg | 480 |
| tcgtggaact | caggcgccct | gaccagcggc | gtgcacacct | tcccggctgt | cctacagtcc | 540 |
| tcaggactct | actccctcag | cagcgtggtg | accgtgccct | ccagcagctt | gggcacgaag | 600 |
| acctacacct | gcaacgtaga | tcacaagccc | agcaacacca | aggtggacaa | gagagttgag | 660 |
| tccaaatatg | gtccccatg | cccacctgc | ccagcacctg | aggccgcgg | ggaccatca | 720 |
| gtcttcctgt | tccccccaaa | acccaaggac | actctcatga | tctcccggac | ccctgaggtc | 780 |
| acgtgcgtgg | tggtggacgt | gagccaggaa | gaccccgagg | tccagttcaa | ctggtacgtg | 840 |
| gatggcgtgg | aggtgcataa | tgccaagaca | aagccgcggg | aggagcagtt | caacagcacg | 900 |
| taccgtgtgg | tcagcgtcct | caccgtcctg | caccaggact | ggctgaacgg | caaggagtac | 960 |
| aagtgcaagg | tctccaacaa | aggcctcccg | tcctccatcg | agaaaaccat | ctccaaagcc | 1020 |
| aaagggcagc | cccgagagcc | acaggtgtac | accctgcccc | catcccagga | ggagatgacc | 1080 |
| aagaaccagg | tcagcctgac | ctgcctggtc | aaaggcttct | accccagcga | catcgccgtg | 1140 |
| gagtgggaaa | gcaatgggca | gccggagaac | aactacaaga | ccacgcctcc | cgtgctggac | 1200 |
| tccgacggct | ccttcttcct | ctacagcagg | ctaaccgtgg | acaagagcag | gtggcaggag | 1260 |
| gggaatgtct | tctcatgctc | cgtgatgcat | gaggctctgc | acaaccacta | cacacagaag | 1320 |
| agcctctccc | tgtctctggg | aggcggagga | tccggggag | ggggttccgg | aggagggggc | 1380 |

```
tcgcaggtgc agctggtgca gtctggggct gaggtgaaga agcctgggtc ctcagtgaag    1440
gtttcctgca aggcatctgg ttacaagttc actgactacc atattcattg ggtgcgacag    1500
gcccctggac aatgccttga gtggatggga gtaattaatc ctacttatgg tactactgac    1560
tacaatcagc ggttcaaagg ccgtgtcacc attaccgcgg acgaatccac gagcacagcc    1620
tacatggagc tgagcagcct gagatctgag gacacggccg tgtattactg tgcgagatat    1680
gattacttta ctgggacggg tgtgtactgg ggccaaggaa ccctggtcac cgtctcctca    1740
ggtggcggag gatctggtgg aggtggctca ggaggtggcg gaagcggcgg aggtggaagt    1800
gatattgtga tgactcagac tccactctcc ctgtccgtca cccctggaca gccggcctcc    1860
atctcctgca gatctagtag gagccttgta cacagtcgtg gagaaaccta tttacattgg    1920
tatctgcaga agccaggcca atctccacag ctcctaattt ataaagtttc caaccggttt    1980
attggggtcc cagacagatt cagcggcagt gggtcaggca cagatttcac actgaaaatc    2040
agcagggtgg aggccgaaga tgttgggggtt tattactgct ctcaaagtac acatcttcca    2100
ttcacgtttg gctgcgggac caagctggag atcaaa                              2136
```

```
<210> SEQ ID NO 4
<211> LENGTH: 642
<212> TYPE: DNA
<213> ORGANISM: Artificial Sequence
<220> FEATURE:
<223> OTHER INFORMATION: synthetic construct

<400> SEQUENCE: 4
gacatccaga tgacccagtc tccatcctcc ctgtctgcat ctgtaggaga cagagtcacc     60
atcacttgcc gggcgagtca gggcattcgc aattatttag cctggtatca gcagaaacca    120
gggaaagctc ctaagctcct gatctatgct gcatccactt tgcaatcagg ggtcccatct    180
cggttcagtg gcagtggatc tgggacagat ttcactctca ccatcagcag cctgcagcct    240
gaagatgttg caacttatta ctgtcaacgc tataaccgtg ccccttacac gttcggccaa    300
gggaccaagg tggaaatcaa acggactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gc                       642
```

ANTI-TNF-ANTI-IL-17 BISPECIFIC ANTIBODIES

The present invention is in the field of medicine, particularly in the novel field of bispecific antibodies directed against Tumor Necrosis Factor alpha (TNFα) and Interleukin-17 (IL-17A). The bispecific antibodies of the present invention are expected to be useful in treating Rheumatoid Arthritis (RA), Psoriatic Arthritis (PsA), and Ankylosing Spondylitis (AS).

RA is a systemic, chronic, inflammatory disease. The inflammation is primarily driven by a multitude of cytokines, including TNFα and IL-17. Current FDA approved bioproducts (e.g., HUMIRA® that bind to and neutralize TNFα have demonstrated efficacy in reducing signs and symptoms of RA and in slowing progression of RA in a subset of patients. IL-17 antibodies are also being studied in clinical trials (secukinumab, ixekizumab, and brodalumab) for various autoimmune diseases, such as rheumatoid arthritis. However, because inflammation is driven by multiple cytokines, it would be advantageous to target two cytokines in a single antibody. It would therefore be advantageous to target both TNFα and IL-17 simultaneously to alleviate inflammation and reduce the immune response in RA patients to a minimum.

Currently, co-administration of a TNFα antibody and anIL-17 antibody requires either injections of two separate products or a single injection of a co-formulation of two different antibodies. Two injections would permit flexibility of dose amount and timing, but are inconvenient to patients both for compliance and for pain. A co-formulation might also provide some flexibility of dose amounts, but it is quite challenging or impossible to find formulation conditions that permit chemical and physical stability of both antibodies due to different molecular characteristics of the two different antibodies. Furthermore, co-administration or co-formulation involves the additive costs of two different drug therapies, which can increase patient and/or payor costs, whereas a single bispecific antibody allows the price to be optimized for the benefit delivered.

WO2010/102251 discloses a dual variable domain immunoglobulin ("DVD-Ig") that binds TNFα and IL-17. A DVD-Ig is a multispecific immunoglobulin that has two identical antigen binding arms with identical specificity and identical CDR sequences, and is bivalent for each antigen to which it binds. Each antigen binding arm has two different variable domains linked in tandem without an intervening constant region between the variable domains, and each variable domain has specificity for a different antigen. WO1995/09917 discloses a method for producing bispecific, tetravalent antibodies using recombinant DNA technology by producing a single chain antibody fused to a complete antibody having a different specificity. This gene fusion is expressed by transfection resulting in a tetravalent antibody having dual specificity. U.S. Pat. No. 6,090,382 discloses human antibodies that bind to and neutralize hTNFα. WO2007/070750 discloses anti-IL-17 antibodies that bind and neutralize human IL-17.

Despite the disclosures above, significant problems associated with chemical and physical stability were encountered when building a bispecific antibody of the present invention. Many changes were required in the starting bispecific antibody to sufficiently overcome myriad issues, including stabilizing the VH/VL interface of the single chain fragment variable region, increasing thermal stability, decreasing aggregation, and rebalancing the electrostatic distribution in the binding surfaces of the bispecific antibody, all while maintaining binding affinity for both antigens.

Therefore, a need still exists for a single bispecific antibody that neutralizes both human TNFα and human IL-17. It is desirable to provide a bispecific antibody that is thermally stable, physically stable, exhibits low aggregation, and neutralizes human TNFα and human IL-17. It is also desirable to provide a pharmaceutical composition including a single bispecific antibody that neutralizes both human TNFα and human IL-17, thereby avoiding the challenges of finding formulation conditions that must satisfy the different molecular characteristics of two different, separate antibodies. The present invention therefore seeks to address one or more of the above mentioned problems.

The present invention provides a bispecific antibody comprising a first polypeptide and a second polypeptide, wherein the first polypeptide has amino acid sequence of SEQ ID NO: 1, and the second polypeptide has an amino acid sequence of SEQ ID NO: 2.

The present invention provides a bispecific antibody comprising two first polypeptides and two second polypeptides, wherein the first polypeptide has amino acid sequence of SEQ ID NO: 1, and the second polypeptide has an amino acid sequence of SEQ ID NO: 2.

The present invention also provides a DNA molecule comprising a polynucleotide sequence encoding the first polypeptide.

The present invention further provides a DNA molecule comprising a polynucleotide sequence encoding the second polypeptide.

The present invention provides a DNA molecule comprising a polynucleotide sequence encoding the first and the second polypeptide.

The present invention also provides a mammalian cell transformed with DNA molecule(s) wherein the cell is capable of expressing a bispecific antibody comprising the first polypeptide and the second polypeptide.

The present invention provides a process for producing a bispecific antibody comprising two first polypeptides and two second polypeptides, the process comprising cultivating the mammalian cell under conditions such that the bispecific antibody is expressed.

The present invention further provides a bispecific antibody produced by said process.

The present invention also provides a method of treating rheumatoid arthritis, psoriatic arthritis, or ankylosing spondylitis comprising administering to a patient in need thereof a therapeutically effective amount of a bispecific antibody according to the present disclosure.

The present invention provides a bispecific antibody according to the present disclosure for use in therapy.

The present invention further provides the use of a bispecific antibody according to the present disclosure for the manufacture of a medicament for use in treatment of rheumatoid arthritis, psoriatic arthritis, or ankylosing spondylitis.

The present invention further provides a bispecific antibody according to the present disclosure for use in the treatment of rheumatoid arthritis, psoriatic arthritis, or ankylosing spondylitis.

The present invention also provides a pharmaceutical composition comprising the bispecific antibody of the present invention and one or more pharmaceutically acceptable carriers, diluents, or excipients.

As used herein, the term "human IL-17" is understood to encompass a homodimeric protein comprising two 15 kD human IL-17A proteins (also known as "human IL-17A"), as well as a heterodimeric protein comprising a 15 kD human IL-17A protein and a 15 kD human IL-17F protein (also known as "human IL-17A/F").

As used herein, the term "bispecific antibody" is understood to comprise two first polypeptides and two second polypeptides as described herein. The bispecific antibody binds two different antigens with specificity for each antigen. The bispecific antibody is capable of binding each antigen alone or each antigen simultaneously. It is further understood that the term encompasses any cellular post-translational modifications to the bispecific antibody including, but not limited to, glycosylation profiles.

The bispecific antibodies of the present invention comprise two first polypeptides and two second polypeptides. One of the first polypeptides forms an inter-chain disulfide bond with one of the second polypeptides. Each of the two first polypeptides forms two inter-chain disulfide bonds with each other, and each of the first polypeptides forms at least one intra-chain disulfide bond. The relationship of the polypeptides and the disulfide bonds are shown in the following schematic for illustrative purposes only:

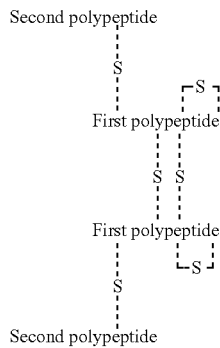

The amino acid sequence of the first polypeptide is:

```
                                              (SEQ ID NO: 1)
EVQLVESGGGLVQPGRSLRLSCAASGFTFDDYAMHWVRQAPGKGLEWVSA

ITWNSGHIDYADSVEGRFTISRDNAKNSLYLQMNSLRAEDTAVYYCAKVS

YLSTASSLDYWGQGTLVTVSSASTKGPSVFPLAPCSRSTSESTAALGCLV

KDYFPEPVTVSWNSGALTSGVHTFPAVLQSSGLYSLSSVVTVPSSSLGTK

TYTCNVDHKPSNTKVDKRVESKYGPPCPPCPAPEAAGGPSVFLFPPKPKD

TLMISRTPEVTCVVVDVSQEDPEVQFNWYVDGVEVHNAKTKPREEQFNST

YRVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGGGG

SGGGGSGGGGSQVQLVQSGAEVKKPGSSVKVSCKASGYKFTDYHIHWVRQ

APGQCLEWMGVINPTYGTTDYNQRFKGRVTITADESTSTAYMELSSLRSE

DTAVYYCARYDYFTGTGVYWGQGTLVTVSSGGGGSGGGGSGGGGSGGGGS

DIVMTQTPLSLSVTPGQPASISCRSSRSLVHSRGETYLHWYLQKPGQSPQ

LLIYKVSNRFIGVPDRFSGSGSGTDFTLKISRVEAEDVGVYYCSQSTHLP

FTFGCGTKLEIK.
```

An expression vector containing the DNA sequence of SEQ ID NO: 3 encodes a first polypeptide having the amino acid sequence of SEQ ID NO: 1.

The amino acid sequence of the second polypeptide is:

```
                                              (SEQ ID NO: 2)
DIQMTQSPSSLSASVGDRVTITCRASQGIRNYLAWYQQKPGKAPKLLIYA

ASTLQSGVPSRFSGSGSGTDFTLTISSLQPEDVATYYCQRYNRAPYTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

An expression vector containing the DNA sequence of SEQ ID NO: 4 encodes a second polypeptide having the amino acid sequence of SEQ ID NO: 2.

An inter-chain disulfide bond of one of the first polypeptides and one of the second polypeptides forms between cysteine residue 135 of SEQ ID NO: 1 and cysteine residue 214 of SEQ ID NO: 2. One first polypeptide forms two inter-chain disulfide bonds with the other first polypeptide. The first inter-chain disulfide bond forms between cysteine residue 227 of the first polypeptide of SEQ ID NO: 1 and cysteine residue 227 of the other first polypeptide of SEQ ID NO: 1. The second inter-chain disulfide bond forms between cysteine residue 230 of the first polypeptide of SEQ ID NO: 1 and cysteine residue 230 of the other first polypeptide of SEQ ID NO: 1.

At least one intra-chain disulfide bond is formed between cysteine residue 505 of SEQ ID NO: 1 and cysteine residue 705 of SEQ ID NO: 1 in each of the first polypeptides.

The first polypeptides comprise a first heavy chain variable region (HCVR1), a heavy chain constant region (CH), a second heavy chain variable region (HCVR2), and a second light chain variable region (LCVR2). The second polypeptides comprise a first light chain variable region (LCVR1) and a light chain constant region (CL). The HCVR and LCVR regions can be further subdivided into regions of hypervariability, termed complementarity determining regions (CDR), interspersed with framework regions (FR). Each HCVR and LCVR is composed of three CDRs and four FRs, arranged from amino-terminus to carboxyl-terminus in the following order: FR1, CDR1, FR2, CDR2, FR3, CDR3, FR4.

The 3 CDRs of HCVR1 are herein referred to as CDRH1-1, CDRH1-2, and CDRH1-3. The 3 CDRs of HCVR2 are referred to as CDRH2-1, CDRH2-2, and CDRH2-3. Likewise, the 3 CDRs of LCVR1 are referred to as CDRL1-1, CDRL1-2, and CDRL1-3, and the 3 CDRs of LCVR2 are referred to as CDRL2-1, CDRL2-2, and CDRL2-3.

The CH is fused to HCVR2 by an amino acid linker (L1). HCVR2 is fused to LCVR2 by an amino acid linker (L2).

The present invention also encompasses diabodies. Diabodies are bispecific antibodies in which HCVR2 and LCVR2 regions are expressed on a single polypeptide chain but instead of the variable domains pairing with complementary domains of the same chain, the variable domains pair with complementary domains of the other chain. For example, if the bispecific antibody comprises two first polypeptides (for convenience, 1A and 1B) and two second polypeptides (for convenience, 2A and 2B), HCVR2 of the 1A polypeptide pairs with complementary domains of LCVR2 of the 1B polypeptide instead of pairing with LCVR2 of the 1A polypeptide, and vice versa. Bispecific diabodies as described herein maintain binding affinity and neutralization capacity for both human TNFα and human IL-17.

Alternatively, it may be beneficial to purify out diabodies from the bispecific antibodies described above. Diabody content can be up to 17% after cellular expression and can be reduced to less than 1% after purification.

The relationship of the various regions and linkers is as follows, arranged from amino-terminus to carboxy-terminus, according to the Kabat numbering convention:

|  | Region | Positions |
| --- | --- | --- |
| Polypeptide 1 - SEQ ID NO: 1 | | |
| HCVR1 | FRH1-1 | 1-25 |
| TNF | CDRH1-1 | 26-35 |
|  | FRH1-2 | 36-49 |
|  | CDRH1-2 | 50-66 |
|  | FRH1-3 | 67-98 |
|  | CDRH1-3 | 99-110 |
|  | FRH1-4 | 111-121 |
| Constant | CH | 122-447 |
| Linker | L1 | 448-461 |
| HCVR2 | FRH2-1 | 462-486 |
| IL-17 | CDRH2-1 | 487-496 |
|  | FRH2-2 | 497-510 |
|  | CDRH2-2 | 511-527 |
|  | FRH2-3 | 528-559 |
|  | CDRH2-3 | 560-569 |
|  | FRH2-4 | 570-580 |
| Linker | L2 | 581-600 |
| LCVR2 | FRL2-1 | 601-623 |
| IL-17 | CDRL2-1 | 624-639 |
|  | FRL2-2 | 640-654 |
|  | CDRL2-2 | 655-661 |
|  | FRL2-3 | 662-693 |
|  | CDRL2-3 | 694-702 |
|  | FRL2-4 | 703-712 |
| Polypeptide 2 - SEQ ID NO: 2 | | |
| LCVR1 | FRL1-1 | 1-23 |
| TNF | CDRL1-1 | 24-34 |
|  | FRL1-2 | 35-49 |
|  | CDRL1-2 | 50-56 |
|  | FRL1-3 | 57-88 |
|  | CDRL1-3 | 89-97 |
|  | FRL1-4 | 98-107 |
| Constant | CL | 108-214 |

Bispecific Antibody Engineering

Significant problems associated with chemical and physical stability were encountered when constructing a bispecific antibody of the present invention. For example, the parental IL-17 antibody exhibited physical stability limitations (e.g., phase separation) at high concentration. Additionally, a bispecific antibody constructed from the parental IL-17 antibody exhibited concentration-dependent self-aggregation. Chemical modifications were therefore made in the CDRL2-1 and CDRH2-2 portions of the bispecific antibody to improve chemical and physical stability and reduce concentration-dependent aggregation. Extensive protein stability and solubility studies in combination with LC/MS identified chemically unstable residues in CDRL2-1 and CDRH2-2. These labile residues were replaced with charge neutral amino acids using targeted libraries constructed by codon depletion. Replacing these labile residues led to improved chemical stability. Additionally, the electrostatic surface of the bispecific antibody was calculated and charged patches were identified. Disrupting these charged patches led to a decrease in protein self-association. Thus, mutations were identified in the CDRH2-1 and CDRL2-1 portions of the bispecific antibody that rebalanced the surface electrostatic distribution, improved thermal stability, reduced aggregation, and improved chemical stability (eliminating specific deamidation and oxidation sites). None of the above modifications were identified in initial characterizations of the parental single antibodies. These changes were encountered only in the context of constructing a bispecific antibody, suggesting that the local environment around the mutated areas of the single antibody differed in the context of a bispecific antibody.

Further chemical modifications were made to reduce bispecific antibody aggregation. In particular, chemical modifications were made to stabilize the VH/VL interface in the IL-17 portion of the bispecific antibody. Studies conducted to determine the driving force behind bispecific antibody aggregation showed that the observed protein self-association was not driven by conformational instability of the individual VH or VL domains, but rather by the opening or "breathing" of the VH-VL interface, leading to intermolecular protein interactions. Thus, various intra-chain disulfide bonds were introduced into the VH-VL interface of the IL-17 portion of the bispecific antibody. One such intra-chain disulfide bond occurs in each of the first polypeptides between cysteine residue 505 of SEQ ID NO: 1 and cysteine residue 705 of SEQ ID NO: 1. This disulfide bond covalently connects the VH and VL interface in the IL-17 portion of the bispecific antibody, which stabilizes the VH-VL interface and reduces intermolecular protein interactions that can lead to physical instability and unfavorable formulation limitations. Out of the nine different disulfide bonds tested, 8 of which expressed functional protein, the magnitude of affinity loss ranged from about 2 to about 35-fold. The intra-chain disulfide bond in each of the first polypeptides between cysteine residue 505 of SEQ ID NO: 1 and cysteine residue 705 of SEQ ID NO: 1 best stabilized the VH/VL interface while maintaining optimal binding affinity for IL-17.

In addition, studies indicated that linker length for L1 affected functional activity of the bispecific antibody, particularly binding kinetics. Kinetic analysis (by surface plasmon resonance) showed that a 10 amino acid linker caused a 2-fold slower $K_{on}$ rate compared to 15 amino acid and 20 amino acid linkers. Thus, a minimum linker length of 15 was introduced into the bispecific antibody of the present invention.

The bispecific antibody of the present invention was also engineered to reduce or eliminate activation of the immune system via interaction with Fcγ receptors Immune activation is not part of the intended mechanism of action of the bispecific antibody of the present invention. To that end, the bispecific antibody of the present invention was constructed as an IgG4 isotype, which is known to have low binding ability to Fcγ receptors or components of the complement system. In addition, two alanine mutations were made in the lower hinge region to further reduce this binding potential.

Bispecific Antibody Binding

The bispecific antibodies of the present invention bind both human TNFα and human IL-17. The bispecific antibodies of the present invention neutralize at least one human TNFα bioactivity and at least one human IL-17 bioactivity in vitro or in vivo. The bispecific antibodies of the present invention are potent inhibitors of IL-17 in vitro, and of both soluble and membrane-bound TNFα in vitro.

The bispecific antibodies of the present invention have a binding affinity ($K_D$) for human TNFα in the range of about 30 pM to about 1 pM, and for human IL-17A in the range of about 40 pM to about 1 pM. Further, the bispecific antibodies of the present invention have a $K_D$ for human IL-17A/F heterodimer of in the range of about 50 pM to about 1 pM. In an aspect, the bispecific antibodies of the present invention have a $K_D$ for human TNFα ranging from about 21 pM to about 3 pM. In another aspect, the bispecific antibodies of the present invention have a $K_D$ for human IL-17A ranging from about 8 pM to about 10 pM.

Bispecific Antibody Expression

Expression vectors capable of directing expression of genes to which they are operably linked are well known in the art. Expression vectors can encode a signal peptide that facilitates secretion of the polypeptide(s) from a host cell. The signal peptide can be an immunoglobulin signal peptide or a heterologous signal peptide. The first polypeptide and the second polypeptide may be expressed independently from different promoters to which they are operably linked in one vector or, alternatively, the first polypeptide and the second polypeptide may be expressed independently from different promoters to which they are operably linked in two vectors—one expressing the first polypeptide and one expressing the second polypeptide.

A host cell includes cells stably or transiently transfected, transformed, transduced, or infected with one or more expression vectors expressing a first polypeptide, a second polypeptide, or both a first polypeptide and a second polypeptide of the invention. Creation and isolation of host cell lines producing a bispecific antibody of the invention can be accomplished using standard techniques known in the art. Mammalian cells are preferred host cells for expression of bispecific antibodies. Particular mammalian cells are HEK 293, NS0, DG-44, and CHO. Preferably, the bispecific antibodies are secreted into the medium in which the host cells are cultured, from which the bispecific antibodies of the present invention can be recovered or purified.

It is well known in the art that mammalian expression of antibodies results in glycosylation. Typically, glycosylation occurs in the Fc region of the antibody at a highly conserved N-glycosylation site. N-glycans typically attach to asparagine. Each of the first polypeptides is glycosylated at asparagine residue 300 of SEQ ID NO: 1.

A particular DNA polynucleotide sequence encoding the first polypeptide having an amino acid sequence of SEQ ID NO: 1 is:

```
                                            (SEQ ID NO: 3)
GAGGTGCAGCTGGTGGAGTCTGGGGGAGGCTTGGTACAGCCTGGGAGGTC

CCTGAGACTCTCCTGTGCAGCCTCTGGATTCACCTTTGATGACTATGCCA

TGCACTGGGTCCGCCAGGCTCCAGGGAAGGGGCTGGAGTGGGTGTCAGCT

ATTACTTGGAATAGTGGTCACATAGACTACGCAGACTCCGTGGAGGGCCG

GTTCACCATCTCCAGAGACAATGCCAAGAACTCCCTGTATCTGCAAATGA

ACAGCCTGAGAGCCGAGGACACGGCCGTATATTACTGTGCGAAAGTGAGC

TACCTGAGTACTGCCTCCAGCCTGGACTACTGGGGCCAAGGAACCCTGGT

CACCGTCTCCTCAGCCTCCACCAAGGGCCCATCGGTCTTCCCGCTAGCGC

CCTGCTCCAGGAGCACCTCCGAGAGCACAGCCGCCCTGGGCTGCCTGGTC

AAGGACTACTTCCCCGAACCGGTGACGGTGTCGTGGAACTCAGGCGCCCT

GACCAGCGGCGTGCACACCTTCCCGGCTGTCCTACAGTCCTCAGGACTCT

ACTCCCTCAGCAGCGTGGTGACCGTGCCCTCCAGCAGCTTGGGCACGAAG

ACCTACACCTGCAACGTAGATCACAAGCCCAGCAACACCAAGGTGGACAA

GAGAGTTGAGTCCAAATATGGTCCCCCATGCCCACCCTGCCCAGCACCTG

AGGCCGCCGGGGACCATCAGTCTTCCTGTTCCCCCCAAAACCCAAGGAC

ACTCTCATGATCTCCCGGACCCCTGAGGTCACGTGCGTGGTGGTGGACGT

GAGCCAGGAAGACCCCGAGGTCCAGTTCAACTGGTACGTGGATGGCGTGG
```
```
                          -continued
AGGTGCATAATGCCAAGACAAAGCCGCGGGAGGAGCAGTTCAACAGCACG

TACCGTGTGGTCAGCGTCCTCACCGTCCTGCACCAGGACTGGCTGAACGG

CAAGGAGTACAAGTGCAAGGTCTCCAACAAAGGCCTCCCGTCCTCCATCG

AGAAAACCATCTCCAAAGCCAAAGGGCAGCCCCGAGAGCCACAGGTGTAC

ACCCTGCCCCCATCCCAGGAGGAGATGACCAAGAACCAGGTCAGCCTGAC

CTGCCTGGTCAAAGGCTTCTACCCCAGCGACATCGCCGTGGAGTGGGAAA

GCAATGGGCAGCCGGAGAACAACTACAAGACCACGCCTCCCGTGCTGGAC

TCCGACGGCTCCTTCTTCCTCTACAGCAGGCTAACCGTGGACAAGAGCAG

GTGGCAGGAGGGGAATGTCTTCTCATGCTCCGTGATGCATGAGGCTCTGC

ACAACCACTACACACAGAAGAGCCTCTCCCTGTCTCTGGGAGGCGGAGGA

TCCGGGGGAGGGGGTTCCGGAGGAGGGGGCTCGCAGGTGCAGCTGGTGCA

GTCTGGGGCTGAGGTGAAGAAGCCTGGGTCCTCAGTGAAGGTTTCCTGCA

AGGCATCTGGTTACAAGTTCACTGACTACCATATTCATTGGGTGCGACAG

GCCCCTGGACAATGCCTTGAGTGGATGGGAGTAATTAATCCTACTTATGG

TACTACTGACTACAATCAGCGGTTCAAAGGCCGTGTCACCATTACCGCGG

ACGAATCCACGAGCACAGCCTACATGGAGCTGAGCAGCCTGAGATCTGAG

GACACGGCCGTGTATTACTGTGCGAGATATGATTACTTTACTGGGACGGG

TGTGTACTGGGGCCAAGGAACCCTGGTCACCGTCTCCTCAGGTGGCGGAG

GATCTGGTGGAGGTGGCTCAGGAGGTGGCGGAAGCGGCGGAGGTGGAAGT

GATATTGTGATGACTCAGACTCCACTCTCCCTGTCCGTCACCCCTGGACA

GCCGGCCTCCATCTCCTGCAGATCTAGTAGGAGCCTTGTACACAGTCGTG

GAGAAACCTATTTACATTGGTATCTGCAGAAGCCAGGCCAATCTCCACAG

CTCCTAATTTATAAAGTTTCCAACCGGTTTATTGGGGTCCCAGACAGATT

CAGCGGCAGTGGGTCAGGCACAGATTTCACACTGAAAATCAGCAGGGTGG

AGGCCGAAGATGTTGGGGTTTATTACTGCTCTCAAAGTACACATCTTCCA

TTCACGTTTGGCTGCGGGACCAAGCTGGAGATCAAA
```

A particular DNA polynucleotide sequence encoding the second polypeptide having an amino acid sequence of SEQ ID NO: 2 is:

```
                                            (SEQ ID NO: 4)
GACATCCAGATGACCCAGTCTCCATCCTCCCTGTCTGCATCTGTAGGAGA

CAGAGTCACCATCACTTGCCGGGCGAGTCAGGGCATTCGCAATTATTTAG

CCTGGTATCAGCAGAAACCAGGGAAAGCTCCTAAGCTCCTGATCTATGCT

GCATCCACTTTGCAATCAGGGGTCCCATCTCGGTTCAGTGGCAGTGGATC

TGGGACAGATTTCACTCTCACCATCAGCAGCCTGCAGCCTGAAGATGTTG

CAACTTATTACTGTCAACGCTATAACCGTGCCCCTTACACGTTCGGCCAA

GGGACCAAGGTGGAAATCAAACGGACTGTGGCTGCACCATCTGTCTTCAT

CTTCCCGCCATCTGATGAGCAGTTGAAATCTGGAACTGCCTCTGTTGTGT

GCCTGCTGAATAACTTCTATCCCAGAGAGGCCAAAGTACAGTGGAAGGTG

GATAACGCCCTCCAATCGGGTAACTCCCAGGAGAGTGTCACAGAGCAGGA

CAGCAAGGACAGCACCTACAGCCTCAGCAGCACCCTGACGCTGAGCAAAG
```

-continued
CAGACTACGAGAAACACAAAGTCTACGCCTGCGAAGTCACCCATCAGGGC

CTGAGCTCGCCCGTCACAAAGAGCTTCAACAGGGGAGAGTGC

Medium, into which a bispecific antibody has been secreted, may be purified by conventional techniques. For example, the medium may be applied to and eluted from a Protein A or G column using conventional methods. Soluble aggregate and multimers may be effectively removed by common techniques, including size exclusion, hydrophobic interaction, ion exchange, or hydroxyapatite chromatography. The product may be immediately frozen, for example at −70° C., or may be lyophilized.

There may be a need to reduce the level of diabody present in the medium. For example, the medium containing the diabody may be applied to and eluted from strong cation exchange resin. For example, SP-Sepharose HP strong cation exchange resin is used to purify correctly-folded bispecific antibody from diabody. The pH of the medium containing the diabody is adjusted to pH 8.1 using 20 mM Bicine. The medium is loaded onto an SP-Sepharose HP column, washed with 2 column volumes of 20 mM Bicine (pH 8.1), and eluted with 20 mM Bicine and 100 mM NaCl (pH 8.1) over 20 column volumes (10-90 mM NaCl). The collected pools can be assessed for high molecular weight versus main peak. A typical result is an improvement from about 17% diabody to less than 1% diabody with about 68% recovery.

Optionally, diabody may be purified according to the following non-limiting procedure: Clarified medium into which the bispecific antibody and diabody have been secreted can be applied to a Protein A affinity column that has been equilibrated with a compatible buffer, such as phosphate buffered saline (pH 7.4). The column can be washed to remove non-specific binding components. The bound bispecific antibody and diabody can be eluted, for example, by pH gradient (such as 0.1 M sodium phosphate buffer pH 6.8 to 0.1 M sodium citrate buffer pH 2.5). The bispecific diabody fractions can be detected by limited lysyl endopeptidase (LysC) digestion to cut between the Fc region and the ScFv/diabody region, followed by reverse phase HPLC quantitative analysis. Briefly, 15 μg of sample can be digested for approximately 20 hours at 37° C. with 0.2 μg of LysC (Wako, P/N 125-05061) in 20 mM Tris pH 8.0+0.1 mg/mL iodoacetamide in a total volume of 50 μL. Samples can be analyzed by injecting 20 μL (6 μg) on a PLRP-S 50×2.1 mm reversed phase column (Varian P/N PL1912-1802). Flow rate can be 0.6 mL/min, column temperature can be 80° C., detection can be at 214 nm, Buffer A can be 0.05% TFA in water, and Buffer B can be 0.04% TFA in acetonitrile. ScFv and diabody peaks (previously identified by LC-MS) can be determined by integrating the appropriate peaks. Material from cation exchange (CEX) chromatography containing the bispecific diabody can be pooled and di-filtered into PBS, pH 7.0. To remove high molecular weight aggregates, the CEX pool can be placed over a Superdex 200 50/60 SEC column run at 7 mL/min in PBS, pH7. The bispecific diabody pool can be determined by SDS-PAGE and analytical SEC analysis. SEC pool can be then diluted 5 fold into the following buffer system: 3.3 mM MES, 3.3 mM Hepes, 3.3 mM Tris, 3.3 mM Bis-Tris Propane, 3.3 mM CHES, 3.3 mM CAPS, pH 5.8. The diluted protein pool can be then loaded onto a preparative ProPAC WCX-10 BioLC cation exchange column (22×250 mm prep scale) at 15 mL/min. Using the buffer system described previously, the bispecific diabody can be separated from bispecific antibody by elution using a linear pH gradient from pH 8.4 to pH 11 at 15 mL/min over 45 minutes collecting 7.5 mL fractions. The ProPac CEX pool made can be based on analytical SEC (TSK3000), analytical CEX (ProPac WCX-10), gel analysis (NuPAGE with MES buffer system), and Lys C digest to measure diabody content in each fraction. The final ProPac CEX pool can be dialyzed into PBS, pH7.

This purification process can remove reduce the diabody content from up to 12% diabody to less than 5% diabody.

Pharmaceutical Compositions and Therapeutic Uses

The bispecific antibody of the invention is expected to treat rheumatoid arthritis, psoriatic arthritis, and ankylosing spondylitis. A "patient" refers to a mammal, preferably a human with a disease, disorder, or condition that would benefit from a decreased level of TNF and/or IL-17 or decreased bioactivity of TNF and/or IL-17.

"Treatment" and/or "treating" are intended to refer to all processes wherein there may be a slowing, interrupting, arresting, controlling, or stopping of the progression of the disorders described herein, but does not necessarily indicate a total elimination of all disorder symptoms. Treatment includes administration of a bispecific antibody of the present invention for treatment of a disease or condition in a mammal, particularly a human, and includes (a) inhibiting further progression of the disease, i.e., arresting its development; and (b) relieving the disease, i.e., causing regression of the disease or disorder, or alleviating symptoms or complications thereof.

The bispecific antibody of the invention can be incorporated into pharmaceutical compositions suitable for administration to a subject. Typically the pharmaceutical composition comprises a bispecific antibody of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Pharmaceutically acceptable carriers may further comprise minor amounts of auxiliary substances that enhance the shelf life or effectiveness of the bispecific antibody.

The compositions of this invention may be in a variety of forms. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In an embodiment, the bispecific antibody is administered by subcutaneous injection. However, as will be appreciated by the skilled artisan, the route and/or mode of administration will vary depending upon the desired results The pharmaceutical compositions of the invention may include a "therapeutically effective amount" of a bispecific antibody of the invention. A "therapeutically effective amount" refers to an amount effective, at dosages and for periods of time necessary, to achieve the desired therapeutic result. A therapeutically effective amount of the bispecific antibody may vary according to factors such as the disease state, age, sex, and weight of the individual, and the ability of the bispecific antibody to elicit a desired response in the individual. A therapeutically effective amount is also one in which any toxic or detrimental effects of the bispecific antibody are outweighed by the therapeutically beneficial effects.

Dosage regimens may be adjusted to provide the optimum desired response (e.g., a therapeutic response). For example, a single bolus may be administered, several divided doses may be administered over time, or the dose may be proportionally reduced or increased as indicated by the exigencies of the therapeutic situation.

Dosage values may vary with the type and severity of the condition to be alleviated. It is further understood that for any particular subject, specific dosage regimens should be adjusted over time according to the individual need and the professional judgment of the person administering or supervising the administration of the compositions.

In another embodiment, the invention provides a method for treating autoimmune diseases, particularly those associated with inflammation, for example rheumatoid arthritis, psoriatic arthritis, and ankylosing spondylitis. Typically, the bispecific antibody is administered systemically, although for certain disorders, local administration of the bispecific antibody at a site of inflammation may be beneficial.

This invention is further illustrated by the following non-limiting example.

EXAMPLE

Expression and Purification of the Bispecific Antibody

The bispecific antibody can be expressed and purified essentially as follows. A glutamine synthetase (GS) expression vector containing the DNA of SEQ ID NO: 3 (encoding the first polypeptide having amino acid sequence of SEQ ID NO: 1) and SEQ ID NO: 4 (encoding the light chain amino acid sequence of SEQ ID NO: 2) is used to transfect the Chinese hamster cell line, CHOK1SV (Lonza Biologics PLC, Slough, United Kingdom) by electroporation. The expression vector encodes an SV Early (Simian Virus 40E) promoter and the gene for GS. Expression of GS allows for the biochemical synthesis of glutamine, an amino acid required by the CHOK1SV cells. Post-transfection, cells undergo bulk selection with 50 pM L-methionine sulfoximine (MSX). The inhibition of GS by MSX is utilized to increase the stringency of selection. Cells with integration of the expression vector cDNA into transcriptionally active regions of the host cell genome are selected against CHOK1SV wild type cells, which express an endogenous level of GS. Transfected pools are plated at low density to allow for close-to-clonal outgrowth of stable expressing cells. The masterwells are screened for bispecific antibody expression and then scaled up in serum-free, suspension cultures to be used for production. Clarified medium, into which the bispecific antibody has been secreted, is applied to a Protein A affinity column that has been equilibrated with a compatible buffer, such as phosphate buffered saline (pH 7.4). The column is washed to remove nonspecific binding components. The bound bispecific antibody is eluted, for example, by pH gradient (such as 0.1 M sodium phosphate buffer pH 6.8 to 0.1 M sodium citrate buffer pH 2.5). Bispecific antibody fractions are detected, such as by SDS-PAGE or analytical size-exclusion, and then are pooled. Soluble aggregate and multimers may be effectively removed by common techniques, including size exclusion, hydrophobic interaction, ion exchange, or hydroxyapatite chromatography. The bispecific antibody may be concentrated and/or sterile filtered using common techniques. The purity of the bispecific antibody after these chromatography steps is greater than 98%. The bispecific antibody may be immediately frozen at −70° C. or stored at 4° C. for several months.

Binding Affinity to TNFα and IL-17
TNFα
Binding affinity of the bispecific antibody to human TNFα is determined using a solution equilibrium binding assay on a Sapidyne KinExA 3000 instrument at 37° C. using Blocker Casein in PBS (Pierce) for running buffer and sample diluent. Human TNFα is immobilized on NHS sepharose through standard amine coupling chemistry. Samples are prepared by mixing the bispecific antibody at a fixed concentration of 20 pM with human TNFα at concentrations of 200, 100, 50, 25, 12.5, 6.25, 3.13, 1.56, 0.78, 0.39, and 0 (blank) pM. Samples are incubated for 18 hours at 37° C. to reach equilibrium prior to analysis. Each analysis cycle consists of (1) packing a column of human TNFα beads by injecting 367 μL of beads at 1 mL/min, (2) injecting 10 mL (20 minute) of bispecific antibody/human TNFα complex over the column at 0.5 mL/min, (3) injecting 0.5 mL (2 minute) of buffer at 0.25 mL/min to wash out unbound sample, (4) injecting 1 mL (30 sec) of 500 ng/mL DyLight-649 Rabbit Anti-Human IgG detection antibody (Jackson ImmunoResearch), (5) injecting 2.25 mL (90 sec) of buffer at 1.5 mL/min to wash out unbound detection antibody, and (6) cleaning the system with a 1 mL (60 sec) injection of 1N NaOH followed by a backflush. Data are fit using N-curve analysis of two replicate experiments using the KinExA Pro Software, version 2.0.1.14. The equilibrium dissociation constant ($K_D$) is calculated from the percent free bispecific antibody. The bispecific antibody of the present invention showed a $K_D$ for human TNFα of 4.4 pM (95% confidence interval of 0.6 to 16.3 pM).

IL-17
Binding affinity of the bispecific antibody to human IL-17 is determined using a surface plasmon resonance assay on a Biacore T200 instrument primed with HBS-EP+(GE Healthcare, 10 mM Hepes pH7.4+150 mM NaCl+3 mM EDTA+0.05% surfactant P20) running buffer and analysis temperature set at 37° C. A CM4 chip containing immobilized protein A (generated using standard NHS-EDC amine coupling) on all four flow cells (Fc) is used to employ a capture methodology. Antibody samples are prepared at 4 μg/mL by dilution into running buffer. Human IL-17 is prepared at final concentrations of 80.0, 40.0, 20.0, 10.0, 5.0, 2.5, 1.25, and 0 (blank) nM by dilution into running buffer. Each analysis cycle consists of (1) capturing antibody samples on separate flow cells (Fc2, Fc3, and Fc4), (2) injecting 200 μL (120 sec) of human IL-17 over all flow cells at 100 μL/min, (3) returning buffer flow for 20 min to monitor dissociation phase, (4) regeneration of chip surfaces with a 10 μL (20 sec) injection of glycine, pH 2.0. Data are processed using standard double-referencing and fit to a 1:1 binding model using Biacore T200 Evaluation software, version 1.0, to determine the association rate ($k_{on}$) and dissociation rate ($k_{off}$). The equilibrium dissociation constant ($K_D$) is calculated as from the relationship $K_D = k_{off}/k_{on}$.

TABLE 1

Binding affinity to human IL-17 by the bispecific antibody.

| Antigen | $k_{on}$ (M$^{-1}$s$^{-1}$) | $k_{off}$ (s$^{-1}$) | $K_D$ (pM) |
|---|---|---|---|
| Human IL-17A | 5.02 ± 0.22 × 10$^6$ | 4.44 ± 0.14 × 10$^{-5}$ | 8.9 ± 0.1 |
| Human IL-17A/F | 2.35 ± 0.00 × 10$^6$ | 5.71 ± 4.95 × 10$^{-5}$ | 42.3 ± 21.1 |

These results demonstrate that the bispecific antibody of the present invention separately can bind human TNFα and human IL-17.

Simultaneous Binding to Human TNFα and Human IL-17
A Biacore T200 instrument is used to determine whether human TNFα and human IL17 can bind to the bispecific antibody simultaneously. All Biacore reagents and materials are purchased from Biacore unless otherwise noted. All measurements are performed at 25° C. HBS-EP+buffer (150 mM sodium chloride, 3 mM EDTA, 0.05% (w/v) surfactant P-20, and 10 mM Hepes, pH 7.4) is used as the running buffer and sample buffer. Protein A is immobilized on flow cells 1 and 2 of a CM4 sensor chip using an amine coupling kit. The bispecific antibody diluted to 3 µg/mL is first captured on flow cell 2 with a 35 second injection at 30 µL/min yielding 165 resonance units (RU) of antibody captured. This capture is followed by a 35 second injection of buffer. The flow rate is then increased to 100 µL/min and flow is directed over flow cell 1 (Fc1) and flow cell 2 (Fc2). To saturate TNFα binding, 50 nM of human TNFα is injected for 2 minutes. Reference-subtracted data are collected as Fc2-Fc1. A binding signal of 45 RU is observed. After human TNFα injection, 80 nM of human IL-17 is injected for an additional 2 minutes to saturate IL-17 binding. Again, reference-subtracted data are collected as Fc2-Fc1. An additional binding signal of 37 RU is observed. The chip surface is then regenerated using 10 mM Glycine, pH 1.5. These results demonstrate that the bispecific antibody of the present invention can bind human TNFα and human IL17 simultaneously, as shown by the increase in resonance units (initial 45 RU from TNFα, then additional 37 RU from human IL-17) from the two ligands binding to the bispecific antibody.

Inhibition of IL-17-Induced CXCL1 Production In Vitro from HT-29 Cells

HT-29 cells are human colorectal adenocarcinoma epithelial cells that naturally express the IL-17 receptor. Incubation of HT-29 cells with human IL-17 results in the production of CXCL1, which can be measured using a commercially available ELISA.

A dose range of the bispecific antibody from 20 pM to 10 nM is evaluated (MW of bispecific antibody is 200 kDa). Each test concentration of bispecific antibody is added (50 µL) to wells containing 50 µL of 2 nM (final concentration) recombinant IL-17. Testing is carried out in duplicate wells per treatment. Assay medium is used for "medium alone" and "IL-17 alone" controls. An IL-17 neutralizing antibody (U.S. Pat. No. 7,838,638) is used as positive control in the assay. Control antibodies are tested at the same molar range as the bispecific antibody. Plates containing IL-17 and antibody mixtures are incubated for 60 to 90 minutes (at 37° C., 95% relative humidity, 5% $CO_2$) in tissue-culture treated 96-well plates.

HT-29 cells are routinely cultured in assay medium (McCoy's 5A containing 10% FBS, penicillinG (0.2 U/mL) and streptomycin (0.2 µg/mL)). The cells are harvested one day before the day of the assay. The cells are rinsed with 1×PBS and detached from the culture flasks with Cell Dissociation buffer, enzyme-free, PBS. Complete assay medium is added to the detached cells. The cells are then centrifuged at 310×g for 5 minutes at room temperature. The cell pellet is resuspended in assay medium. Cell density is measured with Invitrogen Countess, and 20,000 HT-29 cells (in 100 µL) are added to each of the 96-well plates. The 96-well plates are placed in a tissue culture incubator (37° C., 95% relative humidity, 5% $CO_2$) overnight. The antibody/IL-17 mixtures (100 µL) are added to the HT-29 cells and incubated (37° C., 95% relative humidity, 5% $CO_2$) for 24-48 hours.

At the end of the assay, the plates are centrifuged (500×g for 5 minutes at room temperature), and the cell culture medium is transferred to polypropylene 96-well plates, which are sealed and frozen at −80° C. On the day of measuring CXCL1 by ELISA, the plates are thawed at room temperature. CXCL1 levels in medium are measured with a CXCL1 sandwich ELISA (R&D Systems DuoSet #DY275), as per the manufacturer's instructions. At the end of the ELISA reactions, plates are read at 450 nm on a microplate reader (Molecular Devices VersaMax Tunable). Results are expressed as the concentration where 50% of the IL-17-induced response is inhibited ($IC_{50}$) by either bispecific antibody or the positive control is calculated using a 4 parameter sigmoidal fit of the data (GraphPad Prism).

The results demonstrate that the bispecific antibody of the present invention inhibited IL-17-induced secretion of CXCL1 by HT-29 cells in a concentration-dependent manner. The inhibition was comparable to that observed with the positive control antibody [with an $IC_{50}$ for bispecific antibody of 0.628±0.072 nM versus 0.614±0.099 nM for the positive control antibody (average of 3 independent experiments±SEM)], whereas the negative control antibody did not inhibit CXCL1 production. The bispecific antibody of the present invention effectively neutralized IL-17.

Inhibition of TNF-Induced CXCL1 Production In Vitro from HT-29 Cells

HT-29 cells are human colorectal adenocarcinoma epithelial cells that naturally express the TNF receptor. Incubation of HT-29 cells with human TNFα results in the production of CXCL1, which can be measured using a commercially available ELISA.

A dose range of the bispecific antibody from 0.5 pM to 10 nM is evaluated (MW of bispecific antibody is 200 kDa). Each test concentration of bispecific antibody is then added (50 µL) to wells containing 50 µL of 30 pM (final concentration) recombinant TNFα. Testing is carried out in duplicate wells per treatment. Assay medium is used for "medium alone" and "TNF alone" controls. A TNF neutralizing antibody (adalimumab) is used as positive control in the assay. Control antibodies are tested at the same molar range as the bispecific antibody. Plates containing TNFα and antibody mixtures are incubated for 60 to 90 minutes (at 37° C., 95% relative humidity, 5% $CO_2$) in tissue-culture treated 96-well plates.

HT-29 cells are routinely cultured in assay medium (McCoy's 5A containing 10% FBS, penicillinG (0.2 U/mL) and streptomycin (0.2 mcg/mL)). The cells are harvested one day before the day of the assay. The cells are rinsed with 1×PBS and detached from the culture flasks with Cell Dissociation buffer, enzyme-free, PBS. Complete assay medium is added to the detached cells. The cells are then centrifuged at 310×g for 5 minutes at room temperature. The cell pellet is resuspended in assay medium. Cell density is measured with Invitrogen Countess, and 20,000 HT-29 cells (in 100 µL) are added to each of the 96-well plates. The 96-well plates are placed in a tissue culture incubator (37° C., 95% relative humidity, 5% $CO_2$) overnight. The antibody/TNFα mixtures are added to the HT-29 cells and incubated (37° C., 95% relative humidity, 5% $CO_2$) for 24 hours.

At the end of the assay, the plates are centrifuged (500×g for 5 minutes at room temperature), and the cell culture medium is transferred to polypropylene 96-well plates, which are sealed and frozen at −80° C. On the day of measuring CXCL1 by ELISA, the plates are thawed at room temperature. CXCL1 levels in medium are measured with a CXCL1 sandwich ELISA (R&D Systems DuoSet #DY275), as per the manufacturer's instructions. At the end of the ELISA reactions, plates are read at 450 nm on a microplate reader (Molecular Devices VersaMax Tunable). Results are expressed as the concentration where 50% of the TNF-induced response is inhibited ($IC_{50}$) by either bispecific antibody or the positive control is calculated using a 4 parameter sigmoidal fit of the data (GraphPad Prism).

The results demonstrate that the bispecific antibody of the present invention inhibits TNF-induced secretion of CXCL1 by HT-29 cells in a concentration-dependent manner. The inhibition was comparable to that observed with the positive control antibody [with an $IC_{50}$ for bispecific antibody of 18.8±1 pM versus 14.0±2 pM for the positive control antibody (average of 3 independent experiments±SEM)], whereas the negative control antibody did not inhibit CXCL1 production. The bispecific antibody of the present invention effectively neutralized TNFα.

Inhibition of CXCL1 Production from HT-29 Cells Induced by Combination of IL-17 and TNF As described above, HT-29 cells are human colorectal adenocarcinoma epithelial cells that naturally express the IL-17 and TNF receptors. Incubation of HT-29 cells with human TNFα and human IL-17 results in the production of CXCL1, which can be measured using a commercially available ELISA.

The antibodies are tested at a fixed dose of 4 nM (MW of bispecific antibody is 200 kDa). The bispecific antibody is then added (50 μL) to wells containing 50 μL of 3 pM recombinant TNFα and 50 μL of 200 pM recombinant IL-17. Testing is carried out in five replicate wells per treatment. Assay medium is used for "medium alone" and "IL-17+TNF alone". Anti-IL-17 antibody (U.S. Pat. No. 7,838,638); anti-TNFα antibody (adalimumab); and combination of anti-IL-17 antibody/anti-TNF antibody are used as controls in the assay. Control antibodies are tested at the same molar range as the bispecific antibody. Plates containing TNF+IL-17 and antibody mixtures are incubated for 60 to 90 minutes (at 37° C., 95% relative humidity, and 5% $CO_2$) in tissue-culture treated 96-well plates.

HT-29 cells are routinely cultured in assay medium [McCoy's 5A containing 10% FBS, penicillinG (0.2 U/mL) and streptomycin (0.2 mcg/mL)]. The cells are harvested one day before the day of the assay. The cells are rinsed with 1×PBS and detached from the culture flasks with Cell Dissociation buffer, enzyme-free, PBS. Complete assay medium is added to the detached cells. HT-29 cells are then centrifuged at 310×g for 5 minutes at room temperature. The cell pellet is resuspended in assay medium. Cell density is measured with Invitrogen Countess, and 20,000 HT-29 cells (in 100 μL) are added to each of the 96-well plates. The 96-well plates are placed in a tissue culture incubator (37° C., 95% relative humidity, 5% $CO_2$) overnight. The bispecific antibody/IL-17/TNF mixtures are added to the HT-29 cells and incubated (37° C., 95% relative humidity, 5% $CO_2$) for 24-48 h.

At the end of the assay, the plates are centrifuged (500×g for 5 minutes at room temperature), and the cell culture medium is transferred to polypropylene 96-well plates, which are sealed and frozen at −80° C. On the day of measuring CXCL1 by ELISA, the plates are thawed at room temperature. CXCL1 levels in medium are measured with a CXCL1 sandwich ELISA (R&D Systems DuoSet #DY275), as per the manufacturer's instructions. At the end of the ELISA reactions, plates are read at 450 nm on a microplate reader (Molecular Devices VersaMax Tunable). The results are expressed as percent human CXCL1 (with TNF+IL-17 alone being 100%) left after incubation with various antibodies: bispecific antibody 0.85+/−0.12%; anti-TNFα 8.97+/−2.65%; anti-IL-17 27+/−2.07%; anti-TNFα+anti-IL-17 0.59+/−1.23%. The results demonstrated that the bispecific antibody of the present invention inhibited simultaneous TNFα- and IL-17-induced secretion of CXCL1 by HT-29 cells better than the single agents alone.

Inhibition of Soluble TNFα-Induced Cytotoxicity in L929 Cells In Vitro

L929 cells are mouse fibrosarcoma cells that naturally express the TNF receptor. Incubation of L929 cells with human TNFα results in rapid cell death due to excessive formation of reactive oxygen intermediates. The cell death can be measured using an MTT cytotoxicity assay, where mitochondrial succinate dehydrogenase in viable cells reduces tetrazolium salt into formazan product, which can be detected with a fluorescence plate reader.

A dose range of the bispecific antibody from 20 nM to 10 pM is evaluated (MW of bispecific antibody is 200 kDa). Each test concentration of bispecific antibody (100 μL), 200 pg/mL recombinant human TNFα (100 μL), and 6.25 μg/mL Actinomycin-D (100 μL) are added to wells containing L929 cells. Testing is carried out in duplicate wells per treatment. A TNFα neutralizing antibody (adalimumab with IgG4 isotype) is used as a positive control in the assay. Plates containing antibody mixtures are incubated for 60 minutes at room temperature.

L929 cells are routinely cultured in assay medium (1×DMEM Cellgro, 10% FBS, 1% Pen-Strep, 1% MEM essential amino acids, 1% L-glutamine, 1% sodium pyruvate). On the day of the assay, the cells are rinsed with 1×PBS (no $Ca^{++}$ or $Mg^{++}$) and detached from the culture flasks with 0.25% trypsin+EDTA. The trypsin is inactivated with assay medium. L929 cells are centrifuged at 215×g for 5 minutes at room temperature. The cell pellet is resuspended in assay medium. Cell density is measured with a hemocytometer, and 10,000 L929 cells (in 100 μL) are added to the 96-well plates and placed in a tissue culture incubator (37° C., 95% relative humidity, 5% $CO_2$) over night. The antibody/TNFα/actinomycin-D mixture is transferred to the 96 well plates with L929 adherent cells and incubated 18 hrs at 37° C., 95% relative humidity, 5% $CO_2$. The assay medium is removed and the MTT substrate mixture is added to the wells (120 μL). The plates are placed at 37° C., 95% relative humidity, 5% $CO_2$ for 3 hours. The cell death is determined by reading the plates at 490 nm on a microplate reader (Molecular Devices SpectraMax 190). Results are expressed as the concentration where 50% of the TNFα induced response is inhibited ($IC_{50}$) (average of four independent experiments+/−SEM) by either the bispecific antibody or the positive control antibody calculated using a 4 parameter sigmoidal fit of the data (GraphPad Prism).

The results demonstrate that the bispecific antibody of the present invention inhibited TNFα-induced killing of L929 cells in a dose-dependent manner with an $IC_{50}$ of 226+/−52 pM. This inhibition was comparable to that observed with the positive control antibody ($IC_{50}$=243+/−49 pM), whereas the negative control antibody did not inhibit human TNFα. The bispecific antibody of the present invention effectively neutralized human TNFα.

Inhibition of Membrane Bound Human TNFα Induced Cytotoxicity In Vitro in L929 Cells In order to study the ability of the bispecific antibody to inhibit membrane bound TNFα, known cleavage sites of TNFα are inactivated using a set of mutations that were previously demonstrated to allow expression of bioactive TNFα on cell surface (Mueller et. al. 1999) in the absence of TNF cleavage. The non-cleavable TNFα construct is stably transfected to Chinese hamster ovary (CHO) cells. These cells express membrane bound TNFα as shown by flow cytometry. Incubation of L929 cells with CHO cells expressing human non-cleavable membrane bound TNFα results in rapid L929 cell death.

CHO cells expressing membrane bound human TNFα are routinely maintained in selection medium (AM2001 media, an internal CHO growth media without MSX, 8 mM glutamine, GS supplement, HT supplement with 500 μg/mL G418). On the day of the assay, the cells are counted, rinsed with 1×PBS (no $Ca^{++}$ or $Mg^{++}$), centrifuged at 215×g for 5 mM and re-suspended at 50,000 cells/mL in L929 assay medium together with Actinomycin-D (6.25 μg/mL). 500 cells (in 10 μL) of cell suspension are added to each concentration of antibody mixtures that were incubated for 60 minutes at 37° C., 95% relative humidity, 5% $CO_2$. The mixtures containing bispecific antibody, human non-cleavable membrane bound TNFα CHO cells, and Actinomycin-D are transferred to 96-well plates with L929 adherent cells and incubated 18 hours at 37° C., 95% relative humidity, 5% $CO_2$. The cell death is measured using an MTT cytotoxicity assay as described above for soluble TNFα L929 assay. Results are expressed as the concentration where 50% of the TNFα induced response is inhibited ($IC_{50}$) (average of 3 independent experiments+/−SEM) by either the bispecific antibody or the positive control antibody.

The results demonstrate that the bispecific antibody of the present invention inhibited killing of L929 cells by human non-cleavable membrane bound TNFα CHO cells in a dose-dependent manner with an $IC_{50}$ of 646+/−89.5 pM. This inhibition was comparable to that observed with the positive control antibody (adalimumab with IgG4 isotype) ($IC_{50}$=669+/−134 pM), whereas the negative control antibody did not inhibit human TNFα. The bispecific antibody of the present invention effectively neutralized membrane bound human TNFα.

Inhibition of Human IL-17 or TNFα-Induced Production of CXCL1 In Vivo

Injection of human IL-17 or TNFα leads to a rapid and transient increase in mouse CXCL1 in circulation. Regular C57Bl/6J mice (n=7 per group) are injected subcutaneously (16.7 nmol/kg) with the following: (a) bispecific antibody, (b) positive control anti-IL-17 antibody (BAFF/IL-17 bispecific antibody), (c) positive control anti-TNFα antibody (adalimumab with IgG4 isotype); or (d) negative control antibody (human IgG4). Two days later, mice receive a single intraperitoneal injection of human IL-17 (3 μg/mouse) or human TNFα (1 μg/mouse). Two hours after cytokine challenge, the mice are sacrificed and plasma is analyzed for CXCL1 using a commercial ELISA.

TABLE 2

| Average % inhibition of human IL-17- or TNFα-induced CXCL1 production in vivo. | | | |
|---|---|---|---|
| Challenge | Bispecific Ab | Anti-TNFα Ab | Anti-IL-17 Ab |
| IL-17 | 81.9 ± 5 | N/A | 67.3 ± 6 |
| TNFα | 90.5 ± 3 | 89.4 ± 2 | N/A |

The results demonstrate that the bispecific antibody of the present invention significantly inhibited human IL-17- and TNFα-induced CXCL1 production relative to animals that received the negative control antibody (p<0.001, calculated by ANOVA followed by Tukey's Multiple Comparison test). The reduction in CXCL1 production with the bispecific antibody was comparable to that observed with the positive control antibodies. Thus, the bispecific antibody of the present invention effectively neutralized biological effects induced by human IL-17 and TNFα in mouse.

Binding Assays

CD16a, CD32a, and C1q

A 96-well microplate is coated with 100 μL/well of CD32a with a C-terminal 10-His tag (R&D Systems) or recombinant human CD16a with a C-terminal 6-His Tag (R&D Systems) at 1 μg/mL in Phosphate Buffered Saline (PBS). A 96-well microplate is coated with 100 μL/well of human C1q (MP Biologicals) at 2 μg/mL in PBS. The plate is sealed and incubated overnight at 4° C. The coating reagent is removed from each well, and 200 μL/well of casein blocking reagent (Thermo) is added. The plate is sealed and incubated for 1 hour at room temperature (RT). Each well is washed two times with wash buffer (20 mM Tris, 0.15 M NaCl, 0.1% Tween-20, pH 7.5). Serial dilutions of the bispecific antibody of the present invention, human IgG1 positive control, or human IgG4 negative control, all diluted in casein blocking reagent, are added to each well (100 μL/well) and incubated for 2 hours at RT (antibodies are tested with a concentration range of 6.25 to 200 μg/mL in two-fold serial dilutions). Testing is performed in duplicate wells. The plate is then washed three times with wash buffer before 100 μL/well of a 1:12,500 dilution of HRP-conjugated Goat Anti-Human IgG, F(ab')2 (Jackson ImmunoResearch Catalog 109-036-097) in casein blocking reagent is added and incubated for 1 hour at RT. This polyclonal antibody recognizes both human IgG1 and IgG4 (data not shown). The plate is washed four times with wash buffer and TMB Substrate (Pierce, 100 μL/well) is added. Incubation times are 4.5 minutes for CD16a, 9 minutes for CD32a, and 30 minutes for C1q, all in the dark and at RT. Lastly, 100 μL of 1.0 N HCl is added to each well. Optical density is immediately measured using a colormetric microplate reader set to 450 nm.

CD64

A 96-well microplate is coated with 100 μL/well of CD64 with a C-terminal 6-His Tag (R&D Systems) at 1 μg/mL in PBS. The plate is sealed and incubated overnight at 4° C. The coating reagent is removed from each well, and 200 μL/well of casein blocking reagent is added. The plate is sealed and incubated for 1 hour at RT. Each well is washed two times with wash buffer. Serial dilutions of the bispecific antibody of the present invention, human IgG1 positive control, or human IgG4 negative control, all diluted in casein blocking reagent, are added to each well (100 μL/well) and incubated for 1 hour at RT (antibodies are tested with a concentration range of 0.001 to 300 μg/mL in 4-fold serial dilutions). Testing is performed in duplicate wells. The plate is then washed three times with wash buffer before 100 μL/well of a 1:12,500 dilution of HRP-conjugated Goat Anti-Human IgG, F(ab')2 in casein blocking reagent is added and incubated for 1 hour at RT. The plate is washed four times with wash buffer, and 100 μL/well of TMB Substrate is added and incubated for 4.5 minutes in the dark at RT, at which time 100 μL of 1.0 N HCl is added to each well. Optical density is immediately measured using a colormetric microplate reader set to 450 nm.

The results of the in vitro binding experiments show the bispecific antibody of the present invention binding to any of CD16a, CD32a, CD64, or C1q is equal to that observed with the human IgG4 negative control antibody. The human IgG1 positive control antibody binds to all four molecules tested, demonstrating the validity of the assays.

Inhibition of CD4 T Cell and Rheumatoid Arthritis Synoyiocyte Co-Culture-Induced MMP-1, MMP-3, IL-8 and G-CSF Production In Vitro Incubation of activated human CD4 T cells with human fibroblast-like synoviocytes from patients with Rheumatoid Arthritis (RA-FLS) results in the production of inflammatory mediators, such as, MMP-1, MMP-3, IL-8 and G-CSF, and destruction of cartilage and bone. The bispecific antibody of the present invention (Bispecific) (30 nM (based on a MW or 200 kDa)) or a control antibody (Ab) is added in 50 μL to wells containing 50 μL CD4 T Cells (50,000 T cells activated with CD3/CD28 Dynabeads at a 1:1 bead/cell ratio). 100 μL of activated CD4 T cells/with or without an Ab is then added onto RA-FLS plated in 100 μL the night before. Testing is carried out in 8-9 replicate wells per treatment. Human IgG4 Isotype is used as a negative control. IL-17 neutralizing Ab and TNF neutralizing Ab are used as positive controls in the assay. Control Abs were tested at the same molar concentration as the bispecific antibody.

Human PBMC's are isolated using Ficoll-Paque method from a buffy coat [Leuko Reduction System (LRS) chamber], obtained from San Diego Blood Bank. 7 mL LRS product is brought up to 140 mL with PBS. 35 mL of the buffy coat/PBS is overlaid onto 15 mL Ficoll/Histopaque Plus (GE Healthcare). The tubes are balanced and spun at 900×g for 30 minutes at room temperature (RT) without brake. The cell interphase is collected with a serological pipet and washed twice with PBS. Isolated PBMC's are stored at 4° C. overnight in Iscoves Modified Dulbecco's Medium containing 10% FBS, penicillin (100 U/mL), streptomycin (100 U/mL), L-glutamine (100 units/mL) and $5\times10^{-5}$ M 2-beta mercaptoethanol. CD4 T cells are isolated by negative selection (Miltenyi Biotec isolation kit) as per manufacturer's instructions.

RA-FLS cells from Cell Applications, Inc. are routinely cultured in Complete Synoviocyte Growth Medium from Cell Applications, Inc. RA-FLS are harvested one day before the day of the assay. The cells are rinsed with 1×PBS and detached from the culture flasks with Trypsin-EDTA. Complete assay medium is added to the detached cells. RA-FLS are centrifuged at 310×g for 5 minutes at RT. The cell pellet is resuspended in assay medium [Assay medium Dulbecco's Modified Eagle's Medium containing 10% FBS, penicillin G (100 U/mL) and streptomycin (100 U/mL)]. Cell density is measured with Invitrogen Countess, and 10,000 RA-FLS cells (in 100 µL) are added to each well of 96 well plates. The 96 well flat bottom plates are placed in a tissue culture incubator (37° C., 5%).

T cell activation is achieved with Dynabeads coated with anti-CD3 and anti-CD28 (Gibco, Life Technologies). Prior to use, the Dynabeads are washed with an equal amount of wash buffer (PBS with 0.1% bovine serum albumin and 2 mM EDTA, pH 7.4). The beads are placed on a Dynamagnet and after a minute, the supernatant is removed. The beads are removed from the Dynamagnet and resuspended in PBMC media [Iscoves Modified Dulbecco's Medium containing 10% FBS, penicillin (100 U/mL), streptomycin (100 U/mL), L-glutamine (100 units/mL) and $5\times10^{-5}$ M 2-beta mercaptoethanol] to obtain the original bead concentration of $4\times10^7$ beads/mL. 50,000 washed beads in 1.25 µL are added to 50,000 T cells. The bispecific antibody of the present invention or a control antibody (Ab) is added onto CD4 T Cells with CD3/CD28 Dynabeads. The dynabead activated CD4 T cells with or without antibodies are added onto the 96 well plates containing the RA-FLSs. The plates are placed in a tissue culture incubator (37° C., 5% $CO_2$) for 6 days.

At the end of the assay, the plates are centrifuged (500×g for 5 minutes at RT), and the cell culture media is transferred to polypropylene 96-well plates and frozen at −80° C. On the day of measuring MMP-1, MMP-3, IL-8 and G-CSF by ELISA, the plates are thawed at RT. MMP-1, MMP-3, IL-8 and G-CSF levels in media were measured by sandwich ELISA (R&D Systems DuoSet No. DY901, DY513, DY208, DY214, respectively), as per manufacturer's instructions. At the end of the ELISA reactions, plates are read at 450 nm on a microplate reader (Molecular Devices VersaMax Tunable). Results are expressed as cytokine production in ng/mL. Cytokine inhibition with the bispecific antibody of the present invention in activated CD4 T cell: RA-FLS coculture is shown as mean % cytokine left compared to activated CD4 T cell: RA-FLS coculture in the absence of Ab treatment.

|       | IL-17 Ab    | Bispecific | TNF Ab      | Neg Ctrl Ab |
|-------|-------------|------------|-------------|-------------|
| IL-8  | 35.6 ± 17.5 | 12.5 ± 2.6 | 53.4 ± 3.7  | 86.5 ± 18.2 |
| MMP-1 | 61.0 ± 17.5 | 25.1 ± 9.9 | 44.6 ± 13.4 | 83.5 ± 12.7 |
| MMP-3 | 11.9 ± 2.5  | 6.0 ± 4.4  | 56.3 ± 26.1 | 76.1 ± 17.1 |
| G-CSF | 8.8 ± 3.0   | 4.2 ± 0.9  | 62.2 ± 12.1 | 80.3 ± 12.8 |

The bispecific antibody of the present invention inhibited activated human CD4 T cell: RA-FLS co-culture induced production of MMP-1, MMP-3, IL-8 and G-CSF relative to control Abs. The assays were performed three times with similar results.

In Vivo Testing in a Humanized Arthritis Mouse Model

Transgenic expression of human TNF causes spontaneous, progressive inflammatory arthritis in mice (Hayward M. D., et al. BMC Physiology. December 10; 7:13 (2007)). Additional expression of human IL-17 with an Adeno-Associated Virus (AAV) in these mice will further exacerbate spontaneous, progressive polyarthritis. Male human TNF-transgenic mice ((B6.Cg(SJL)-Tg(TNF) N21, Taconic Farms, Georgetown, N.Y., model 1006) carry the entire human TNFα gene including a promoter and a stabilized 3'UTR that results in low constitutive expression of human TNFα in all tissues Animals are housed 2/cage with free access to food and water. A standardized scoring system is used to score their arthritic disease in front and hind paws (Front Paw: 0=no evidence of distortion or swelling, 1=mild swelling of the ankle, 2=moderate swelling or mild distortion, 3=severe swelling or severe distortion, 4=severe swelling and severe distortion. Hind paw: 0=no evidence of distortion or swelling, 1=mild distortion/inability to spread toes straight, 2=moderate distortion/inability to spread toes, 3=severe medial contortion/mild swelling, 4=severe medial contortion with marked swelling). At 8 weeks of age mice are intravenously injected (100 uL/mouse via tail vein) with $1\times10^{10}$ genomic copies of Adeno-associated virus (AAV) carrying a gene for human IL-17 (n=32) or an irrelevant gene (lacz, n=8). Viral expression of human IL-17 is detected in mouse plasma obtained from tail snips using a commercial ELISA kit (Meso Scale Discovery, Rockville, Md.) according to the manufacturer's instructions. The average plasma levels are about 500 pg/ml human IL-17. At 12 weeks of age the mice are randomized into study groups based on their clinical arthritis score, human IL-17 plasma levels, and body weight. Treatment with the different antibodies is initiated on the day of grouping Animals are dosed weekly, subcutaneously for 9 weeks with 2 different doses (20 and 3.3 nmol/kg) of the bispecifc antibody of the present invention (Bispecific) or TNF neutralizing antibody (TNF Ab) or an isotype control antibody (Neg Ctrl Ab) (20 nmol/kg). Clinical arthritis scores are determined routinely in a blinded fashion. At termination plasma is obtained by cardiac puncture, hind legs are fixed in 10% formalin. The hind legs are demineralized in EDTA, trimmed, processed in the routine manner, embedded in paraffin, sectioned, and stained with hematoxylin and eosin. Arthritis scoring is conducted for the following categories: Inflammation, bone resorption, cartilage damage, and pannus formation on a scale of 0-5: 0=normal, 1=minimal, 2=mild, 3=moderate, 4=marked, 5=severe for a potential total of 20.

All antibodies are formulated in PBS at an appropriate concentration to result in a 200 uL/mouse subcutaneous dose.

Average Histology Scores of Hindpaws of Human TNF Transgenic/IL-17 Mice after Treatment

| | Group | | | | |
|---|---|---|---|---|---|
| | Neg Ctrl Ab | Bispecific | | TNF Ab | |
| Dose | 20 nmol/kg | 20 nmol/kg | 3.3 nmol/kg | 20 nmol/kg | 3.3 nmol/kg |
| Histology Score (0-20) day 63 | 12.3 ± 2.0 | 0.5 ± 0.2*** | 2.8 ± 0.5** | 1.0 ± 0.4*** | 7.8 ± 2.3 |

***$p < 0.001$,
**$p < 0.01$ versus Neg Ctrl Ab (one way ANOVA). Histology scores are cumulative of the four different parameters (Inflammation, bone resorption, cartilage damage, and pannus formation scored at a scale from 0-5).

This data demonstrates the bispecific antibody of the present invention is effective in a disease model of human cytokine-driven disease.

In Vivo Testing of a Humanized Psoriasis Mouse Model

A humanized mouse model of psoriasis is a model that involves grafting of human non-lesional skin biopsies from psoriasis patients onto the back skin of immunodeficient mice. After the human skin has grafted (3 to 4 weeks later), T-cell activated human peripheral blood mononuclear cells (PBMCs) from the same donor are intradermally injected into the graft to induce psoriasis-like epidermal thickening (Wrone-Smith and Nickoloff J., Clin Invest. 15; 98(8):1878-87 (1996)).

Mice (10-27/group) are treated once weekly with the bispecific antibody of the present invention (Bispecific) (66.6, 3.3 or 0.67 nmol/kg), TNF neutralizing antibody (TNF Ab) (66.6 or 3.3 nmol/kg), PBS or betamethasone (twice daily topical), starting the day before the PBMC injection. After three weeks the mice are euthanized, the grafted skin was isolated, and the thickness of the epidermis is measured.

The bispecific antibody of the present invention (66.6 nmol/kg) significantly reduced epidermal thickening in the human skin grafts compared to PBS control (p=0.047). The bispecific antibody of the present invention (66.6 nmol/kg) was able to reduce the epidermal thickening in the human skin grafts better than TNF Ab (66.6 nmol/kg) (p=0.0057). These results demonstrate efficacy of the bispecific antibody of the present invention in a humanized mouse model of psoriasis.

Mean Epidermal Thickness

| Group | Mean (μm) | SD | n | SEM |
|---|---|---|---|---|
| Pre-transplantation | 59.8 | 12.1 | 27 | 2.3 |
| PBS | 111.9 | 34.0 | 27 | 6.5 |
| Betamethasone | 74.9 | 23.4 | 10 | 7.4 |
| TNF Ab 66.6 nmol/kg | 121.7 | 29.5 | 10 | 9.3 |
| TNF Ab 3.3 nmol/kg | 122.7 | 42.1 | 11 | 12.7 |
| Bispecific 66.6 nmol/kg | 82.7 | 26.7 | 10 | 8.4 |
| Bispecific 3.3 nmol/kg | 91.9 | 19.7 | 2 | 57 |
| Bispecific 0.67 nmol/kg | 132.5 | 77.1 | 10 | 24.4 |

Stability Analysis

The bispecific antibody is formulated in 10 mM citrate+150 mM NaCl, pH 6. The bispecific antibody is concentrated at 100 mg/mL using Amicon Ultra-4 30,000 MWCO concentrators (Millipore). Tween-80 is added to a final concentration of 0.02% (v/v). Concentrated samples are stored at 25° C. over a period of 4 weeks. Samples are analyzed for percent high molecular weight (% HMW) with size exclusion chromatography (SEC) at time zero, after 1 week, and after 4 weeks. SEC is performed on an Agilent 1100 system using a TSK G3000SW-XL (Tosoh Bioscience) column 50 mM sodium phosphate+0.35 M NaCl, pH 7.0 is used as the mobile phase running at 0.5 mL/min for 35 minutes. A volume of 1 uL of the concentrated bispecific antibody is injected into the column and monitored at 280 nm. Chromatograms are analyzed using ChemStation, and % HMW is calculated using the ratio of AUC of the peaks eluted before the monomer peak to total AUC. Samples stored at 25° C. at different time points are analyzed for % HMW. At time zero, % HMW was 1.52; at 1 week, % HMW was 2.01; and at 4 weeks, % HMW was 2.37.

The results demonstrate that the bispecific antibody of the present invention is stable as there was no significant change in soluble aggregate after 4 weeks.

Sequences
HC-ScFv:

SEQ ID NO: 1
EVQLVESGGGLVQPGRSLRLSCAASGFTFDDYAMHWVRQAPGKGLEWVSA

ITWNSGHIDYADSVEGRFTISRDNAKNSLYLQMNSLRAEDTAVYYCAKVS

YLSTASSLDYWGQGTLVTVSSASTKGPSVFPLAPCSRSTSESTAALGCLV

KDYFPEPVTVSWNSGALTSGVHTFPAVLQSSGLYSLSSVVTVPSSSLGTK

TYTCNVDHKPSNTKVDKRVESKYGPPCPPCPAPEAAGGPSVFLFPPKPKD

TLMISRTPEVTCVVVDVSQEDPEVQFNWYVDGVEVHNAKTKPREEQFNST

YRVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGGGG

SGGGGSGGGGSQVQLVQSGAEVKKPGSSVKVSCKASGYKFTDYHIHWVRQ

APGQCLEWMGVINPTYGTTDYNQRFKGRVTITADESTSTAYMELSSLRSE

DTAVYYCARYDYFTGTGVYWGQGTLVTVSSGGGGSGGGGSGGGGSGGGGS

DIVMTQTPLSLSVTPGQPASISCRSSRSLVHSRGETYLHWYLQKPGQSPQ

LLIYKVSNRFIGVPDRFSGSGSGTDFTLKISRVEAEDVGVYYCSQSTHLP

FTFGCGTKLEIK

LC:
SEQ ID NO: 2
DIQMTQSPSSLSASVGDRVTITCRASQGIRNYLAWYQQKPGKAPKLLIYA

ASTLQSGVPSRFSGSGSGTDFTLTISSLQPEDVATYYCQRYNRAPYTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

HC-ScFv:
SEQ ID NO: 3
GAGGTGCAGCTGGTGGAGTCTGGGGGAGGCTTGGTACAGCCTGGGAGGTC
CCTGAGACTCTCCTGTGCAGCCTCTGGATTCACCTTTGATGACTATGCCA
TGCACTGGGTCCGCCAGGCTCCAGGGAAGGGGCTGGAGTGGGTGTCAGCT
ATTACTTGGAATAGTGGTCACATAGACTACGCAGACTCCGTGGAGGGCCG
GTTCACCATCTCCAGAGACAATGCCAAGAACTCCCTGTATCTGCAAATGA
ACAGCCTGAGAGCCGAGGACACGGCCGTATATTACTGTGCGAAAGTGAGC
TACCTGAGTACTGCCTCCAGCCTGGACTACTGGGGCCAAGGAACCCTGGT
CACCGTCTCCTCAGCCTCCACCAAGGGCCCATCGGTCTTCCCGCTAGCGC
CCTGCTCCAGGAGCACCTCCGAGAGCACAGCCGCCCTGGGCTGCCTGGTC
AAGGACTACTTCCCCGAACCGGTGACGGTGTCGTGGAACTCAGGCGCCCT
GACCAGCGGCGTGCACACCTTCCCGGCTGTCCTACAGTCCTCAGGACTCT
ACTCCCTCAGCAGCGTGGTGACCGTGCCCTCCAGCAGCTTGGGCACGAAG
ACCTACACCTGCAACGTAGATCACAAGCCCAGCAACACCAAGGTGGACAA
GAGAGTTGAGTCCAAATATGGTCCCCCATGCCCACCCTGCCCAGCACCTG
AGGCCGCCGGGGGACCATCAGTCTTCCTGTTCCCCCCAAAACCCAAGGAC
ACTCTCATGATCTCCCGGACCCCTGAGGTCACGTGCGTGGTGGTGGACGT
GAGCCAGGAAGACCCCGAGGTCCAGTTCAACTGGTACGTGGATGGCGTGG
AGGTGCATAATGCCAAGACAAAGCCGCGGGAGGAGCAGTTCAACAGCACG
TACCGTGTGGTCAGCGTCCTCACCGTCCTGCACCAGGACTGGCTGAACGG
CAAGGAGTACAAGTGCAAGGTCTCCAACAAAGGCCTCCCGTCCTCCATCG
AGAAAACCATCTCCAAAGCCAAAGGGCAGCCCCGAGAGCCACAGGTGTAC
ACCCTGCCCCCATCCCAGGAGGAGATGACCAAGAACCAGGTCAGCCTGAC
CTGCCTGGTCAAAGGCTTCTACCCCAGCGACATCGCCGTGGAGTGGGAAA
GCAATGGGCAGCCGGAGAACAACTACAAGACCACGCCTCCCGTGCTGGAC
TCCGACGGCTCCTTCTTCCTCTACAGCAGGCTAACCGTGGACAAGAGCAG
GTGGCAGGAGGGGAATGTCTTCTCATGCTCCGTGATGCATGAGGCTCTGC
ACAACCACTACACACAGAAGAGCCTCTCCCTGTCTCTGGGAGGCGGAGGA
TCCGGGGGAGGGGGTTCCGGAGGAGGGGGCTCGCAGGTGCAGCTGGTGCA
GTCTGGGGCTGAGGTGAAGAAGCCTGGGTCCTCAGTGAAGGTTTCCTGCA
AGGCATCTGGTTACAAGTTCACTGACTACCATATTCATTGGGTGCGACAG
GCCCCTGGACAATGCCTTGAGTGGATGGGAGTAATTAATCCTACTTATGG
TACTACTGACTACAATCAGCGGTTCAAAGGCCGTGTCACCATTACCGCGG
ACGAATCCACGAGCACAGCCTACATGGAGCTGAGCAGCCTGAGATCTGAG
GACACGGCCGTGTATTACTGTGCGAGATATGATTACTTTACTGGGACGGG
TGTGTACTGGGGCCAAGGAACCCTGGTCACCGTCTCCTCAGGTGGCGGAG
GATCTGGTGGAGGTGGCTCAGGAGGTGGCGGAAGCGGCGGAGGTGGAAGT
GATATTGTGATGACTCAGACTCCACTCTCCCTGTCCGTCACCCCTGGACA
GCCGGCCTCCATCTCCTGCAGATCTAGTAGGAGCCTTGTACACAGTCGTG
GAGAAACCTATTTACATTGGTATCTGCAGAAGCCAGGCCAATCTCCACAG
CTCCTAATTTATAAAGTTTCCAACCGGTTTATTGGGGTCCCAGACAGATT
CAGCGGCAGTGGGTCAGGCACAGATTTCACACTGAAAATCAGCAGGGTGG
AGGCCGAAGATGTTGGGGTTTATTACTGCTCTCAAAGTACACATCTTCCA
TTCACGTTTGGCTGCGGGACCAAGCTGGAGATCAAA

LC:
SEQ ID NO: 4
GACATCCAGATGACCCAGTCTCCATCCTCCCTGTCTGCATCTGTAGGAGA
CAGAGTCACCATCACTTGCCGGGCGAGTCAGGGCATTCGCAATTATTTAG
CCTGGTATCAGCAGAAACCAGGGAAAGCTCCTAAGCTCCTGATCTATGCT
GCATCCACTTTGCAATCAGGGGTCCCATCTCGGTTCAGTGGCAGTGGATC
TGGGACAGATTTCACTCTCACCATCAGCAGCCTGCAGCTGAAGATGTTG
CAACTTATTACTGTCAACGCTATAACCGTGCCCCTTACACGTTCGGCCAA
GGGACCAAGGTGGAAATCAAACGGACTGTGGCTGCACCATCTGTCTTCAT
CTTCCCGCCATCTGATGAGCAGTTGAAATCTGGAACTGCCTCTGTTGTGT
GCCTGCTGAATAACTTCTATCCCAGAGAGGCCAAAGTACAGTGGAAGGTG
GATAACGCCCTCCAATCGGGTAACTCCCAGGAGAGTGTCACAGAGCAGGA
CAGCAAGGACAGCACCTACAGCCTCAGCAGCACCCTGACGCTGAGCAAAG
CAGACTACGAGAAACACAAAGTCTACGCCTGCGAAGTCACCCATCAGGGC
CTGAGCTCGCCCGTCACAAAGAGCTTCAACAGGGGAGAGTGC

We claim:

1. An anti-TNF-anti-IL-17 bispecific antibody comprising a first polypeptide and a second polypeptide, wherein the first polypeptide has amino acid sequence of SEQ ID NO: 1, and the second polypeptide has an amino acid sequence of SEQ ID NO: 2.

2. The bispecific antibody of claim 1 comprising two first polypeptides and two second polypeptides.

3. A method of treating rheumatoid arthritis, psoriatic arthritis, or ankylosing spondylitis comprising administering to a patient in need thereof a therapeutically effective amount of a bispecific antibody of claim 2.

4. A pharmaceutical composition comprising the bispecific antibody of claim 2 and one or more pharmaceutically acceptable carriers, diluents, or excipients.

5. An anti-TNF-anti-IL-17 bispecific antibody produced by cultivating a mammalian cell that comprises a polynucleotide sequence encoding the polypeptide having the amino acid sequence of SEQ ID NO:1 and a polynucleotide sequence encoding the polypeptide having the amino acid sequence of SEQ ID NO:2 under conditions such that the polypeptides are expressed, and recovering the bispecific antibody.

6. A pharmaceutical composition comprising the bispecific antibody of claim 5 and one or more pharmaceutically acceptable carriers, diluents or excipients.

* * * * *